US012286645B2

(12) United States Patent
Abdelalim et al.

(10) Patent No.: US 12,286,645 B2
(45) Date of Patent: Apr. 29, 2025

(54) GENERATION OF INDUCED PLURIPOTENT STEM CELLS (IPSCs) WITH GLUT2 MUTATION OR FOXA2 DELETION, METHODS OF PREPARING SAME, AND METHODS OF USING SAME

(71) Applicant: Qatar Foundation for Education, Science and Community Development, Doha (QA)

(72) Inventors: Essam M. Abdelalim, Doha (QA); Ahmed K. Elsayed, Doha (QA); Khalid Hussain, Doha (QA)

(73) Assignee: HAMAD BIN KHALIFA UNIVERSITY, Doha (QA)

( * ) Notice: Subject to any disclaimer, the term of this patent is extended or adjusted under 35 U.S.C. 154(b) by 2 days.

(21) Appl. No.: 17/161,269

(22) Filed: Jan. 28, 2021

(65) Prior Publication Data

US 2021/0230557 A1    Jul. 29, 2021

Related U.S. Application Data

(60) Provisional application No. 62/966,875, filed on Jan. 28, 2020.

(51) Int. Cl.
  *C12N 5/074*  (2010.01)
  *C12N 15/64*  (2006.01)
  *G01N 33/50*  (2006.01)

(52) U.S. Cl.
  CPC .......... *C12N 5/0696* (2013.01); *C12N 15/64* (2013.01); *C12N 2510/00* (2013.01)

(58) Field of Classification Search
  CPC .. C12N 5/0696; C12N 15/64; C12N 2510/00; C12N 2506/11; G01N 33/5073
  See application file for complete search history.

(56) References Cited

U.S. PATENT DOCUMENTS

2019/0282710 A1   9/2019  Fussenegger et al.

FOREIGN PATENT DOCUMENTS

CN        109563487 A       4/2019

OTHER PUBLICATIONS

Sharari (Understanding the Role of GLUT2 in Dysglycemia Associated with Fanconi-Bickel Syndrome. Biomedicine, vol. 10, Aug. 2022) (Year: 2022).*
Griscelli (Generation an induced pluripotent stem cell (iPSC) line from a patient with maturity-onset diabetes of the young type (MODY13) with a the potassium inwardly-rectifying channel, subfamily J, member 11(KCNJ11) mutation. Stem Cell Research, vol. 23, Jul. 2017) (Year: 2017).*
Dweikat (Fanconi-Bickel syndrome in two Palestinian children: marked phenotypic variability with identical mutation. BMC Research Notes, vol. 9, Aug. 2016). (Year: 2016).*
NM_00040.2 (Year: 2000).*
Santer et al (The mutation spectrum of the facilitative glucose transporter gene SLC2A2 (GLUT2) in patients with Fanconi-Bickel syndrome. Hum Genet (2002) 110 :21-29) (Year: 2002).*
NM 000340.2 (Year: 2018).*
Abbasi et al., "Segregation of a Novel Homozygous 6 Nucleotide Deletion in GLUT2 Gene in a Fanconi-Bickel Syndrome Family", Gene (2015), 557(1), pp. 103-105.
Al-Haggar et al., "Mutation Analysis of the GLUT2 Gene in Three Unrelated Egyptian Families with Fanconi-Bickel Syndrome: Revisited Gene Atlas for Renumbering", Clinical and Experimental Nephrology (2012), 16(4), pp. 604-610.
Ang et al., "HNF-3β is Essential for Node and Notochord Formation in Mouse Development", Cell (1994), 78(4), pp. 561-574. (Abstract only).
Barroso et al., "Candidate Gene Association Study in Type 2 Diabetes Indicates a Role for Genes Involved in β-Cell Function as Well as Insulin Action", PLoS Biology (2003), 1(1), pp. 41-55.
Elsayed et al., "An Induced Pluripotent Stem Cell Line Derived from a Patient with Neonatal Diabetes and Fanconi-Bickel Syndrome Caused by a Homozygous Mutation in the SLC2A2 Gene", Stem Cell Research (2021), 54(10), pp. 1-5.
Elsayed et al., "Generation of a Human Induced Pluripotent Stem Cell Line (QBRli009-A) from a Patient with a Heterozygous Deletion of FOXA2", Stem Cell Research (2020), vol. 42, pp. 1-5.
Enogieru et al., "Functional and Structural Analysis of Rare SLC2A2 Variants Associated with Fanconi-Bickel Syndrome and Metabolic Traits", Human Mutation (2019), 40(7), pp. 983-995.
Gao et al., "Foxa1 and Foxa2 Maintain the Metabolic and Secretory Features of the Mature β-cell", Molecular Endocrinology (2010), 24(8), pp. 1594-1604.
Gaulton et al., "Genetic Fine Mapping and Genomic Annotation Defines Causal Mechanisms at Type 2 Diabetes Susceptibility Loci", Nature Genetics (2015), 47(12), pp. 1415-1425.
Guillam et al., "Early Diabetes and Abnormal Postnatal Pancreatic Islet Development in Mice Lacking Glut-2", Nature Genetics (1997), 17(3), pp. 327-330. (Abstract only).
Heddad-Masson et al., "Foxa1 and Foxa2 Regulate α-Cell Differentiation, Glucagon Biosynthesis, and Secretion", Endocrinology (2014), 155(10), pp. 3781-3792.
Kaestner et al., "Inactivation of the Winged Helix Transcription Factor HNF3α Affects Glucose Homeostasis and Islet Glucagon Gene Expression in vivo", Genes & Development (1999), 13(4), pp. 495-504.

(Continued)

*Primary Examiner* — Emily A Cordas
*Assistant Examiner* — Matasha Dhar
(74) *Attorney, Agent, or Firm* — K&L Gates LLP

(57) ABSTRACT

The present disclosure generally relates to the method of generating human induced pluripotent stem cells (hiPSC) from patients with either heterozygous deletion of the FOX2A gene or GLUT2 (SLC2A2) gene mutations. The methods disclosed herein generate human cell models for diabetes, Fanconi Bickel Syndrome (FBS), dysmporphic features, growth hormone deficiency, central hypothyroidism, and related disorders. The methods disclosed herein generate patient-specific iPSC cell lines that could be used by researchers to perform mechanistic studies, drug screening, and understanding the role of GLUT2 or FOXA2 in specific human cell types.

2 Claims, 16 Drawing Sheets
(5 of 16 Drawing Sheet(s) Filed in Color)

(56) References Cited

OTHER PUBLICATIONS

Lantz et al., "Foxa2 Regulates Multiple Pathways of Insulin Secretion", The Journal of Clinical Investigation (2004), 114 (4), pp. 512-520.
Laukkanen et al., "Polymorphisms in the SLC2A2 (GLUT2) Gene are Associated with the Conversion from Impaired Glucose Tolerance to Type 2 Diabetes: The Finnish Diabetes Prevention Study", Diabetes (2005), 54(7), pp. 2256-2260.
Mannstadt et al., "Fanconi-Bickel Syndrome and Autosomal Recessive Proximal Tubulopathy with Hypercalciuria (ARPTH) are Allelic Variants Caused by GLUT2 Mutations", The Journal of Clinical Endocrinology & Metabolism (2012), 97(10), pp. E1978-E1986.
Møller et al., "Studies of Genetic Variability of the Glucose Transporter 2 Promoter in Patients with Type 2 Diabetes Mellitus", The Journal of Clinical Endocrinology & Metabolism (2001), 86(5), pp. 2181-2186.
Sansbury et al., "SLC2A2 Mutations Can Cause Neonatal Diabetes, Suggesting GLUT2 May Have a Role in Human Insulin Secretion", Diabetologia (2012), 55(9), pp. 2381-2385.
Santer et al., "Fanconi-Bickel Syndrome—A Congenital Defect of Facilitative Glucose Transport", Current Molecular Medicine (2002), 2(2), pp. 213-227. (Abstract only).
Scott et al., "Large-Scale Association Analyses Identify New Loci Influencing Glycemic Traits and Provide Insight into the Underlying Biological Pathways", Nature Genetics (2012), 44(9), pp. 991-1005.
Segev et al., "The Expression of the Class 1 Glucose Transporter Isoforms in Human Embryonic Stem Cells, and the Potential Use of GLUT2 as a Marker for Pancreatic Progenitor Enrichment", Stem Cells and Development (2012), 21 (10), pp. 1653-1661. (Abstract only).
Shih et al., "Impaired Glucose Homeostasis and Neonatal Mortality in Hepatocyte Nuclear Factor 3α-Deficient Mice", Proceedings of the National Academy of Sciences of the United States of America (1999), 96(18), pp. 10152-10157.
Soranzo et al., "Common Variants at 10 Genomic Loci Influence Hemoglobin A1C Levels via Glycemic and Nonglycemic Pathways", Diabetes (2010), 59(12), pp. 3229-3239.
Stanley, C.A., "Perspective on the Genetics and Diagnosis of Congenital Hyperinsulinism Disorders", The Journal of Clinical Endocrinology and Metabolism (2016), 101(3), pp. 815-826.
Weinstein et al., "The Winged-Helix Transcription Factor HNF-3β is Required for Notochord Development in the Mouse Embryo", Cell (1994), 78(4), pp. 575-588. (Abstract only).
Willmann et al., "The Global Gene Expression Profile of the Secondary Transition During Pancreatic Development", Mechanisms of Development (2016), vol. 139, pp. 51-64.

\* cited by examiner

Translocation between the short arm of chromosome 6 and 20. karyotype: [46 XY, t (6; 20)(p11;p11)] and a deletion (46, XY, del(20)(p11.21p11.22).

*In vitro* differentiation

Scorecard technique

GENERATION OF INDUCED PLURIPOTENT STEM CELLS (IPSCs) WITH GLUT2 MUTATION OR FOXA2 DELETION, METHODS OF PREPARING SAME, AND METHODS OF USING SAME

RELATED APPLICATIONS

This application claims to the benefit of U.S. Provisional Patent Application No. 62/966,875, filed on Jan. 28, 2020, the entire contents of which are incorporated by reference herein.

TECHNICAL FIELD

The present disclosure generally relates to induced pluripotent stem cells (iPSC) from patients with either a heterozygous deletion of the FOX2A gene or GLUT2 (SLC2A2) gene mutations and methods of generating the induced pluripotent stem cells. The methods disclosed herein generate human cell models for diabetes, Fanconi Bickel Syndrome (FBS), dysmorphic features, growth hormone deficiency, central hypothyroidism, and related disorders.

BACKGROUND

It has been reported that mutations in the GLUT2 (SLC2A2) gene can lead to neonatal diabetes and increase the risk of developing type 2 diabetes (T2D). Sansbury, F. H., et al (2012) *SLC2A2 mutations can cause neonatal diabetes, suggesting GLUT2 may have a role in human insulin secretion*, Diabetologia 55:2381-2385; Barroso, I., et al (2003) *Candidate gene association study in type 2 diabetes indicates a role for genes involved in beta-cell function as well as insulin action*, PLoS Biol 1:E20; Soranzo, N., et al (2010) *Common variants at 10 genomic loci influence hemoglobin A(1)(C) levels via glycemic and nonglycemic pathways*, Diabetes 59:3229-3239; Scott, R. A., et al (2012) *Large-scale association analyses identify new loci influencing glycemic traits and provide insight into the underlying biological pathways*, Nat Genet 44:991-1005. A previous study reported that recessive mutations in the SLC2A2 gene lead to neonatal diabetes, before the appearance of the clinical features of FBS, which is caused by homozygous mutations or compound heterozygous mutations in GLUT2. Sansbury, 2012; Santer, R., et al (2002) *Fanconi-Bickel syndrome—a congenital defect of facilitative glucose transport*, Curr Mol Med 2:213-227; Abbasi, F., et al (2015) *Segregation of a novel homozygous 6 nucleotide deletion in GLUT2 gene in a Fanconi-Bickel syndrome family*, Gene 557:103-105; Mannstadt, M., et al (2012) *Fanconi-Bickel syndrome and autosomal recessive proximal tubulopathy with hypercalciuria (ARPTH) are allelic variants caused by GLUT2 mutations*, J Clin Endocrinol Metab 97:E1978-1986; Al-Haggar, M., et al (2012) *Mutation analysis of the GLUT2 gene in three unrelated Egyptian families with Fanconi-Bickel syndrome: revisited gene atlas for renumbering*, Clin Exp Nephrol 16:604-610. This indicates that a single unaffected allele is enough to fulfil essential protein functions. More than 70% of mutations lead to truncated proteins (nonsense, splice site mutations, frameshift) or inactive proteins. A previous study on Finland population found that in the GLUT2 gene, SNPs rs5393 (AA) and rs5394 (CC) (promoter region) and SNPsrs5400 (T110I) and rs5404 (GG, T198T) (exon region) can predict the conversion from impaired glucose tolerance (IGT) in obese individuals to T2D. Furthermore, the risk of T2D is increased three times due to rs5393 (AA). Barroso, 2003. SLC2A2 knockout mice have severe diabetes and die within 3 weeks after birth due to a defect in insulin secretion. Guillam, M. T., et al (1997) *Early diabetes and abnormal postnatal pancreatic islet development in mice lacking Glut-2*, Nat Genet 17:327-330. It has been reported that GLUT2 is the main glucose transporter in mice beta cells. In adult human beta cells, it has been reported that GLUT2 may not be the main glucose transporter indicating that its role in T2D is still not clear. Barroso, 2003; Laukkanen, O., et al (2005) *Polymorphisms in the SLC2A2 (GLUT2) gene are associated with the conversion from impaired glucose tolerance to type 2 diabetes: the Finnish Diabetes Prevention Study*, Diabetes 54:2256-2260; Moller, A. M., et al (2001) *Studies of genetic variability of the glucose transporter 2 promoter in patients with type 2 diabetes mellitus*, J Clin Endocrinol Metab 86:2181-2186. Currently, there is no human model that can recapitulate the diabetes and FBS phenotypes of GLUT2 mutations.

FOXA proteins perform distinct functions as evident in the phenotypes of mouse models. Foxa2 knockout mice die at early an embryonic stage and showed developmental defects in the foregut and neural tube; however, Foxa3 knockout mice are normal. Kaestner, K. H., et al (1999) *Inactivation of the winged helix transcription factor HNF3alpha affects glucose homeostasis and islet glucagon gene expression in vivo*, Genes Dev 13:495-504; Weinstein, D. C., et al (1994) *The winged-helix transcription factor HNF-3 beta is required for notochord development in the mouse embryo*, Cell 78:575-588; Ang, S. L. and Rossant, J. (1994) *HNF-3 beta is essential for node and notochord formation in mouse development*, Cell 78:561-574. Foxa1 knockout mice develop hormonal deficiency, neonatal hypoglycemia, islet dysfunction in alpha and beta cells and die within two weeks after birth. Kaestner, 1999; Shih, D. Q., et al (1999) *Impaired glucose homeostasis and neonatal mortality in hepatocyte nuclear factor 3alpha-deficient mice*, Proc Natl Acad Sci USA 96:10152-10157. Studies on animal models showed that Foxa2 is involved in insulin secretion in mature beta cells. Specific deletion of Foxa2 in beta cells leads to hypoglycemia in a mouse model. Gao, N., et al (2010) *Foxa1 and Foxa2 maintain the metabolic and secretory features of the mature beta-cell*, Mol Endocrin 24:1594-1604. It has been reported that Foxa2 regulates several genes involved in insulin secretion, including KCNJ11 and ABCC8 encoding Kir6.2 and Sur1 subunits of the ATP-sensitive potassium channel in beta cells. Heddad Masson, M., et al (2014) *Foxa1 and Foxa2 regulate alphacell differentiation, glucagon biosynthesis, and secretion*, Endocrin 155:3781-3792. Genetic mutations in those genes lead to congenital hyperinsulinism. Stanley, C. A. (2016) *Perspective on the Genetics and Diagnosis of Congenital Hyperinsulinism Disorders*, J Clin Endocrinol Metab 101:815-826. During pancreatic development, FOXA2 is expressed at very early stages starting from the endodermal stage; however, its protein level is upregulated during the endocrine progenitor stage. Willmann, S. J., et al (2016) *The global gene expression profile of the secondary transition during pancreatic development*, Mech Dev 139:51-64. The exocrine and ductal cells have low expression of FOXA2. Id. Furthermore, it plays an important role in maintaining the functionality of mature pancreatic beta cells. Gao, 2014; Lantz, K. A., et al (2004) *Foxa2 regulates multiple pathways of insulin secretion*, J Clin Invest 114:512-520. In beta cells, FOXA2 deletion results in hyperinsulinemia due to defects in the insulin secretion. Lantz, 2004. Recently, in human, T2D risk alleles have been found to be associated with FOXA2-bound enhancers. Gaulton, K. J., et al (2015) *Genetic fine mapping and genomic annotation defines causal mechanisms at type 2 diabetes susceptibility loci*, Nat Gen 47:1415-1425. Since Foxa2 knockout mice die at early embryonic stage, a haploinsufficient FOXA2 model would provide a tool to study the role of FOXA2 during development.

SUMMARY

Disclosed herein are human iPSCs (hiPSCs) and human iPSC-derived differentiated cells useful as models for various metabolic diseases related to genetic lesions in either FOXA2 or GLUT2.

One aspect provides a method for generating hiPSC containing a heterozygous deletion of FOXA2 by exposing patient-derived peripheral blood mononuclear cells (PBMC) containing a heterozygous deletion of FOXA2 to means for inducing pluripotency. Some embodiments further comprise a step for differentiating the iPSCs to generate an isolated population of cells of a specific type.

One aspect provides an isolated population of hiPSCs containing a heterozygous deletion of FOXA2.

One aspect provides an isolated population of differentiated cells derived from the hiPSC containing a heterozygous deletion of FOXA2. In one embodiment the differentiated cells are B cells. In one embodiment, the differentiated cells are skeletal muscle cells. In one embodiment, the differentiated cells are liver cells. In one embodiment, the differentiated cells are neuronal cells. In one embodiment, the differentiated cells are pancreatic cells.

In some embodiments, the hiPSC or differentiated cells containing a heterozygous deletion of FOXA have a 969 Kb deletion of chromosome 20 at bands p11.22 to p11.21.

On aspect provides a method for generating hiPSC containing inactivating mutations in both copies of GLUT2 by exposing patient-derived peripheral blood mononuclear cells (PBMCs) containing inactivating mutations in both copies of GLUT2 to means for inducing pluripotency. Some embodiments further comprise a step for differentiating the hiPSCs to generate an isolated population of cells of a specific type.

One aspect provides an isolated population of hiPSC containing inactivating mutations in both copies of GLUT2.

One aspect provides an isolated population of differentiated cells derived from the hiPSCs containing inactivating mutations in both copies of GLUT2. In one embodiment the differentiated cells are pancreatic beta cells. In one embodiment, the differentiated cells are skeletal muscle cells. In one embodiment, the differentiated cells are liver cells.

In some embodiments, the hiPSCs containing inactivating mutations in both copies of GLUT2 have a nonsense c.901C>T mutation in exon 6 of the SLC2A2 gene (NM_000340), resulting in p.Arg301Ter. In some embodiments, the hiPSCs containing inactivating mutations in both copies of GLUT2 have a mutation for c.613-7T>G: IVS5-7T>G in intron 5 in the SLC2A2 gene. In some embodiments, the inactivating mutations are homozygous.

In various embodiments, the disclosed hiPSC and hiPSC-derived differentiated cells are useful in researching the development and pathologies related to diabetes, Fanconi Bickel Syndrome (FBS), dysmporphic features, growth hormone deficiency, dopamine neurons, central hypothyroidism, and related disorders. Some embodiments comprise a method of screening drugs by exposing differentiated cells derived for the hiPSC to a library of drug candidates.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Definitions

Figure 1:
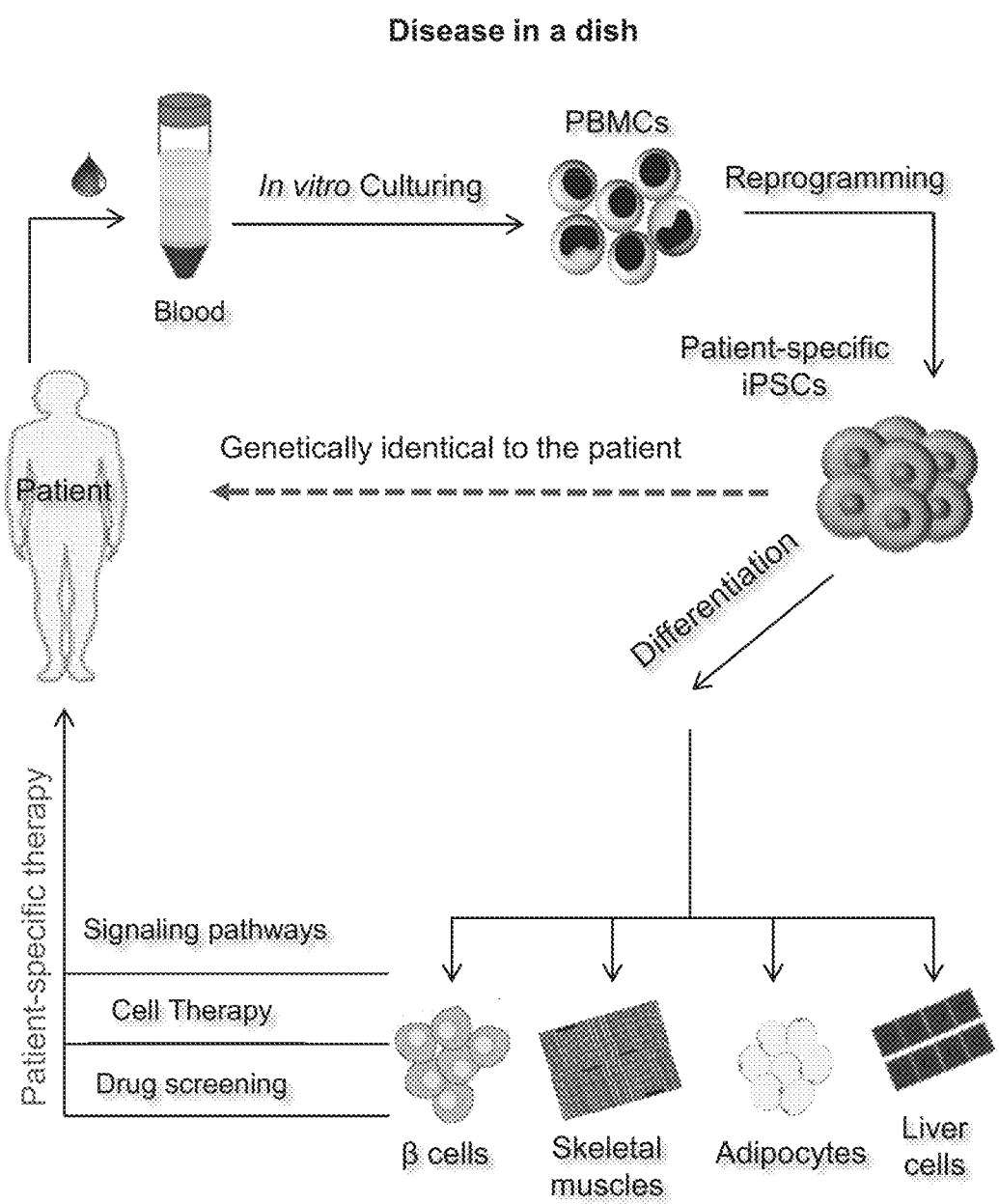
FIG. 1 shows a general scheme for generating patient-specific hiPSCs and hiPSC-derived differentiated cells from a patient.
Figure 2:
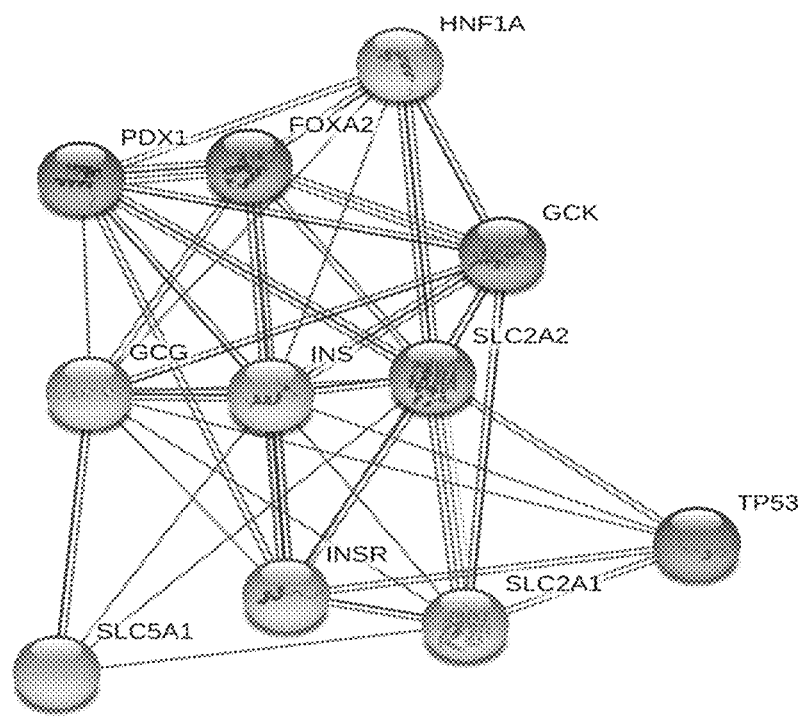
FIG. 2 shows the SLC2A2 protein interaction network. SLC2A2 encodes for GLUT2, a glucose transporter gene. SLC2A2 is expressed in liver, intestine, kidney, and pancreatic islet beta cells, as well as the central nervous system, in neurons and astrocytes. Inactivating mutations in GLUT2 cause FBS, which is characterized by hepatomegaly and kidney disease; defects in insulin secretion are rare in adult patients.

Some definitions are provided hereafter. Nevertheless, definitions may be located in the "Embodiments" section below, and the above header "Definitions" does not mean that such disclosures in the "Embodiments" section are not definitions.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y."

Where used herein, the terms "example" and "such as," particularly when followed by a listing of terms, are merely exemplary and illustrative and should not be deemed to be exclusive or comprehensive.

The term "isolated" means altered or removed from a natural state. For example, a protein naturally present in a living animal is not "isolated," while the same protein partially or completely separated from all or some of the coexisting materials of its natural state is "isolated."

A "subject" or "individual" is a mammal, preferably a human. As used herein, an "effective amount" is an amount of a compound, formulation, material, composition, or a combination of such, that treats a disease or medical condition in an individual, or, more generally, reduces symptoms, manages progression of the disease or disorder or reduces the disease burden. Herein, "effective amount" and "therapeutically effective amount" are used interchangeably.

The terms "peptide" or "protein" or "polypeptide" refers to a polymer of amino acid residues covalently linked by peptide bonds. The terms "peptides" or "proteins" or "polypeptides," used herein, may also refer to a polymer of amino acids where one or more of the amino acids may be a modified residue, such as an artificial amino acid mimetic or a synthetic amino acid residue. The terms "peptide" or "protein" or "polypeptide" are used interchangeably.

The term "amino acid" refers to both naturally occurring and synthetic amino acids as well as analogs and amino acid mimetics. Herein, amino acids are referred to by the standard IUB/IUPAC amino acid codes, including both one-letter and three-letter codes.

The terms "nucleic acid" or "genetic material" or "polynucleotide" refers to "deoxyribonucleic acid" (DNA) or "ribonucleic acid" (RNA) and polymers thereof, in either single- or double-stranded form.

The terms "treatment" and "treat" include both prophylactic or preventive treatment (that prevent and/or slow the development of a targeted pathologic condition, infection, disorder, or disease) and curative, therapeutic or disease-modifying treatment, including therapeutic measures that cure, slow down, lessen symptoms of, and/or halt progression of a diagnosed pathologic condition, infection, disorder, or disease. The terms "treatment" and "treat" do not necessarily imply that a subject is treated until total recovery. The terms "treatment" and "treat" are also intended to include the potentiation or otherwise enhancement of one or more primary prophylactic or therapeutic measures. As non-limiting examples, a treatment can be performed by a doctor, a healthcare professional, a veterinarian, a veterinarian professional, or another human.

The term "unit dosage form," as used herein, refers to physically discrete units suitable as unitary dosages for subjects, each unit containing a predetermined quantity of the composition disclosed herein in amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

The term "sterile" is understood to mean free from any bacteria or other living microorganisms.

The term "pharmaceutically acceptable" as used herein refers to substances that do not cause substantial adverse allergic or immunological reactions when administered to a subject.

All percentages expressed herein are by weight of the total weight of the composition unless expressed otherwise. When reference herein is made to the pH, values correspond to pH measured at about 25° C. with standard equipment. "Ambient temperature" or "room temperature" is between about 15° C. and about 25° C., and ambient pressure is about 100 kPa.

The term "mM", as used herein, refers to a molar concentration unit of an aqueous solution, which is mmol/L. For example, 1.0 mM equals 1.0 mmol/L.

The terms "substantially no," "essentially free" or "substantially free" as used in reference to a particular component means that any of the component present constitutes no more than about 3.0% by weight, such as no more than about 2.0% by weight, no more than about 1.0% by weight, preferably no more than about 0.5% by weight or, more preferably, no more than about 0.1% by weight.

One aspect provides a method for generating human iPSC containing a heterozygous deletion of FOXA2 by exposing patient-derived peripheral blood mononuclear cells (PBMC) containing a heterozygous deletion of FOXA2 to means for inducing pluripotency. Another aspect provides a method for generating hiPSC containing inactivating mutations in both copies of GLUT2 by exposing patient-derived peripheral blood mononuclear cells (PBMC) containing inactivating mutations in both copies of GLUT2 to means for inducing pluripotency. By pluripotent it is meant that the cells can differentiate into a full range of cell types. This should not be confused with multipotent stem cells (also called adult or somatic stem cells) which can differentiate only into a limited number of cell types. Additionally, hiPSCs are distinct from human embryonic stem cells, typically derived from in vitro fertilized ova, rather than from somatic cells. Due to this difference in origin, the gene expression profiles of these two types of human pluripotent cells differ. Populations of hiPSCs with a high level of enrichment or purity, typically 95-100%, can be obtained in vitro. Such populations do not occur in the human body.

PBMCs are reprogrammed according to methods known to those of skill in the art. Briefly, PBMC can be prepared by density gradient sedimentation of blood in, for example, a Ficoll gradient. The PBMC can then be cultured for several days (for example, 5 days) in an appropriate media (for example, StemPro-34 media with cytokines). The actual reprograming entails expression of certain protein factors in the PBMC often involving use of a viral vector. Multiple vector systems are known in the art, including retroviral systems that require integration of the vector(s) into the host genome; DNA-based vectors such as adenovirus, adeno-associated virus, and plasmid vectors, which do not require integration into the host genome, but may nonetheless integrate; and non-integrating vectors, such as Sendai virus vectors (Sendai is a cytoplasmic RNA virus). One particular Sendai virus system is commercially available as CYTO-TUNE™ Sendai Reprograming Kit. The particular reprogramming factors expressed by this kit are OCT Sox2, Klf4, and c-Myc (sometime referred to as Yamanaka factors). Other combinations of reprogramming factors are known in the art. Such factors, vectors to express them, and associated cell culture reagents constitute means for reprogramming. The vectors are transduced into the somatic cells to be reprogrammed which are cultured for several days in a first medium appropriate to the cell type being reprogrammed (PBMC, fibroblasts, etc.). They are then transferred to plates with feeder layer (for example, mouse embryo fibroblasts) or vitronectin-coated plates (or other matrix-coated plates, e.g., Matrigel) and a 2nd medium is used. Some protocols entail a gradient transition to a third medium. Colonies of hiPSC emerge, often at around 12 days after transduction. After a total of 2-4 weeks the colonies are considered ready for transfer, expansion, and characterization.

HiPSCs can be characterized by multiple techniques to confirm their identity, including immunostaining, RT-PCR, Western blotting, karyotyping, alkaline phosphatase, and direct and spontaneous differentiation. Pluripotency markers that are expressed by hiPSCs include OCT4, SOX2, NANOG, SSEA4, TRA60 and TRA81. HiPSCs show a human embryonic stem cell-like morphology, stain positive for alkaline phosphatase, can differentiate into the three germ layers, ectoderm, mesoderm, and endoderm, and should have a normal karyotype.

Some embodiments further comprise a step for differentiating the iPCS (carrying either a FOXA2 lesion or a GLUT2 lesion) to generate an isolated population of cells of a specific type. Differentiation is influenced by the substrate the hiPSC are cultured on and the selection of supplements, growth factors, and cytokines present in the culture medium, as is known to one of skill in the art and, often, commercially available.

One aspect provides an isolated population of hiPSC containing a heterozygous deletion of FOXA2. Complete absence of FOXA2 is an embryonic lethal condition. The present embodiments retain one, but not two, functional copies of the FOXA2. In some embodiments the FOXA2 gene has been deleted. In one particular embodiment, there is a deletion of chromosome 20 at bands p11.22 to p11.21. In some embodiments, this deletion is 969 Kb.

One aspect provides an isolated population of differentiated cells derived from the hiPSC that retain one, but not two, functional copies of the FOXA2. The retention of the one functional copy overcomes the developmental lethality of the absence of FOXA2, to allow the generation of differentiation cells with defects related to the lack of FOXA2. Some embodiments provide isolated population of differentiated cells containing a heterozygous deletion of FOXA2. In one embodiment the differentiated cells are pancreatic beta and alpha cells. In one embodiment, the differentiated cells are skeletal muscle cells. In one embodiment, the differentiated cells are liver cells. In one embodiment, the differentiated cells are lung cells. In one embodiment, the differentiated cells are neuronal cells (e.g., dopaminergic neurons). In one embodiment, the differentiated cells are pancreatic cells. In some embodiments the FOXA2 gene has been deleted. In one particular embodiment, there is a deletion of chromosome 20 at bands p11.22 to p11.21. In some embodiments, this deletion is 969 Kb.

One aspect provides an isolated population of hiPSC containing inactivating mutations in both copies of GLUT2. One aspect provides an isolated population of differentiated cells derived from the hiPSC containing inactivating mutations in both copies of GLUT2. In some embodiments, the hiPSCs containing inactivating mutations in both copies of GLUT2, or the differentiated cells derived therefrom, have a mutation in exon 6 of the SLC2A2 gene (NM_000340), causing a substitution of a single nucleotide (C to T) at position 901 in the coding region (c.901C>T). This mutation results in a change in one codon from encoding the amino acid Arginine to a termination codon (p.Arg301Ter). In some embodiments, the hiPSC containing inactivating mutations in both copies of GLUT2, or the differentiated cells derived therefrom, have a mutation in intron 5 of the SLC2A2 gene, causing a substitution of a single nucleotide (T to G) at position 613 (c.613-7T>G: IVS5-7T>G). In some embodiments, the inactivating mutations are heterozygous. In other embodiments the inactivating mutations are homozygous.

With respect to the various aspects described above, in some embodiments the isolated population has a purity of cell type of at least 95%. In various embodiments, the isolated population comprises at least $10^4$, $5 \times 10^4$, $10^5$, $2 \times 10^5$, $5 \times 10^5$, $8 \times 10^5$, $10^6$, $2 \times 10^6$, or $5 \times 10^6$ cells. As the hiPSC have high telomerase activity, they have virtually unlimited ability to proliferate so that very large number of hiPSCs can be obtained.

To study FBS associated with SLC2A2 mutations, the hiPSCs with GLUT2 mutations can be differentiated into hepatic cells to study the mechanism of hepatomegaly associated with glycogen accumulation in the hepatic cells. Also, they can be differentiated into kidney cells (renal tubules) to understand the mechanism of renal tubule dysfunction.

For drug screening, GLUT2 mutated hiPSCs or FOXA2$^{+/-}$hiPSCs can be differentiated into target cells, including pancreatic beta cells, neuronal cells, hepatic cells, and kidney cells among others. Those differentiated cells contain the genetic defects associated with GLUT2 mutations; therefore, one can test several drugs or perform drug screening on those cells to identify novel drugs that can reverse the disease phenotypes.

GLUT2 mutated hiPSCs are particularly useful for the study of Fanconi Bickel syndrome (FBS) and monogenic diabetes.

FOXA2$^{+/-}$ hiPSCs are particularly useful for the study of diabetes, hyperinsulinism, hypopituitarism and craniofacial and endoderm-derived organ abnormalities.

EXAMPLES

The following non-limiting examples support the concept of generating patient-specific hiPSCs with GLUT2 mutations or a heterozygous deletion of the FOX2A gene.

Example 1

Figure 3:
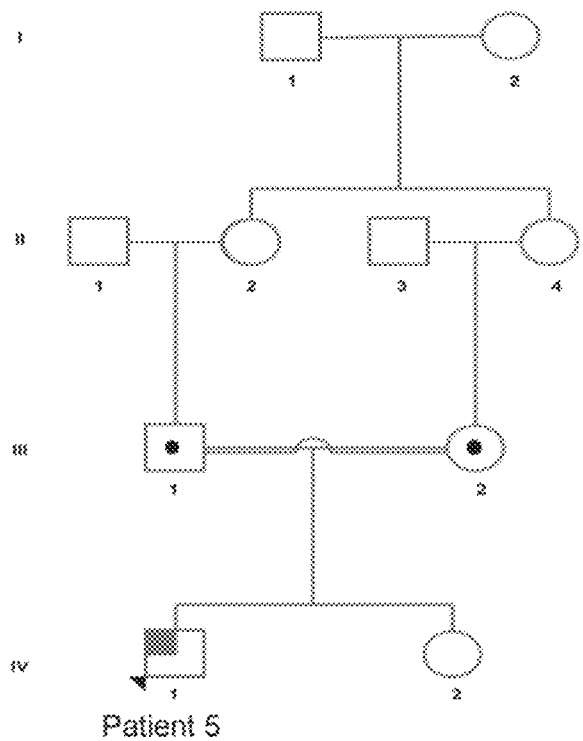
FIG. 3 shows the family pedigree of Patient #1 (individual IV-1) with GLUT2 mutation.
Figure 5:
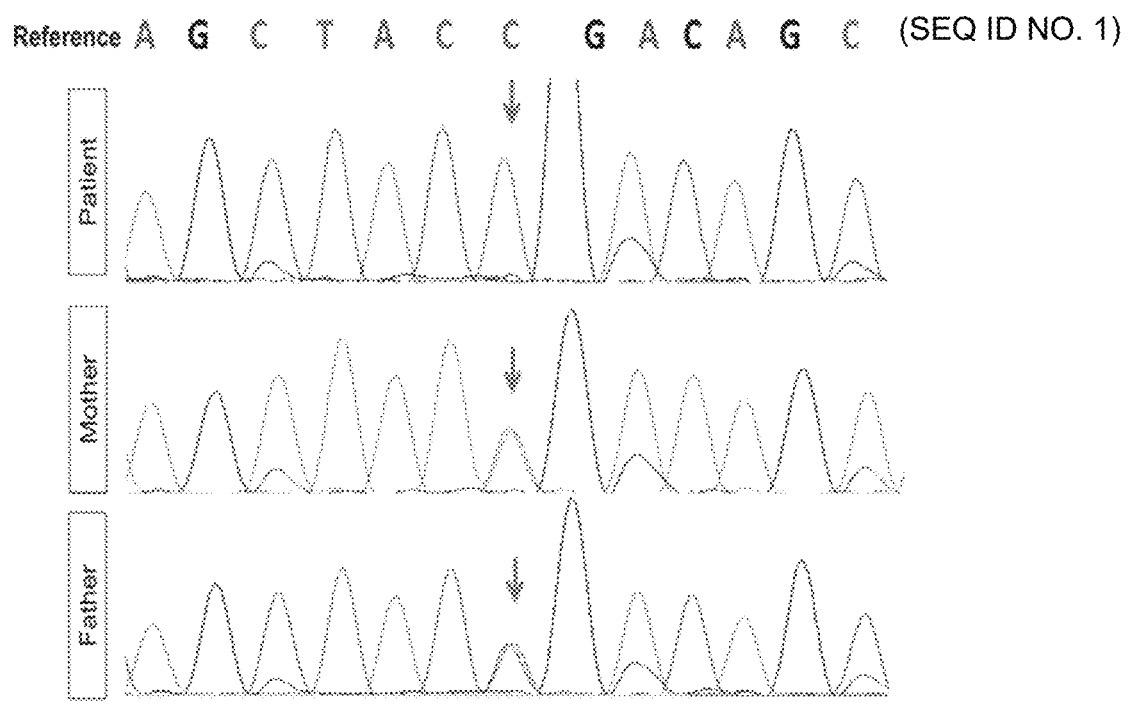
FIG. 5 shows the whole exome sequencing (WES) analysis which was performed on Patient #1 (individual IV-1) with a GLUT2 mutation. WES analysis revealed a homozygous c.901C>T mutation in exon 6 of the SLC2A2 gene (NM_000340), resulting in p.Arg301Ter.

A study identified two patients who presented with mutations in GLUT2. Patient #1 was a 24-month-old boy with FBS and severe proximal tubular dysfunction with failure to thrive and marked short stature. At 4 days of age, newborn screening revealed a mild increase in total galactose with normal galactose-1-phosphate uridylyl transferase (GALT) enzyme activity and all forms of Galactosaemia were excluded. At 18 days of life, the patient has displayed characteristic biochemical findings of fasting hypoglycemia and postprandial hyperglycemia, a hallmark seen in FBS, with an elevated Hba1c level of 6.7% and low C-peptide level diagnostic of PNDM. Patient #1's family pedigree is shown in FIG. 3. Patient #1's GLUT2 mutation was confirmed by whole exome sequencing (WES) as shown in FIG. 5. WES analysis was performed at two months of age detecting a homozygous c.901C>T mutation in exon 6 of the SLC2A2 gene (NM_000340), resulting in p.Arg301Ter. Both parents were heterozygous carriers (FIG. 5). The SLC2A2 mutation identified is expected to result in a truncated GLUT2 protein.

Figure 4:
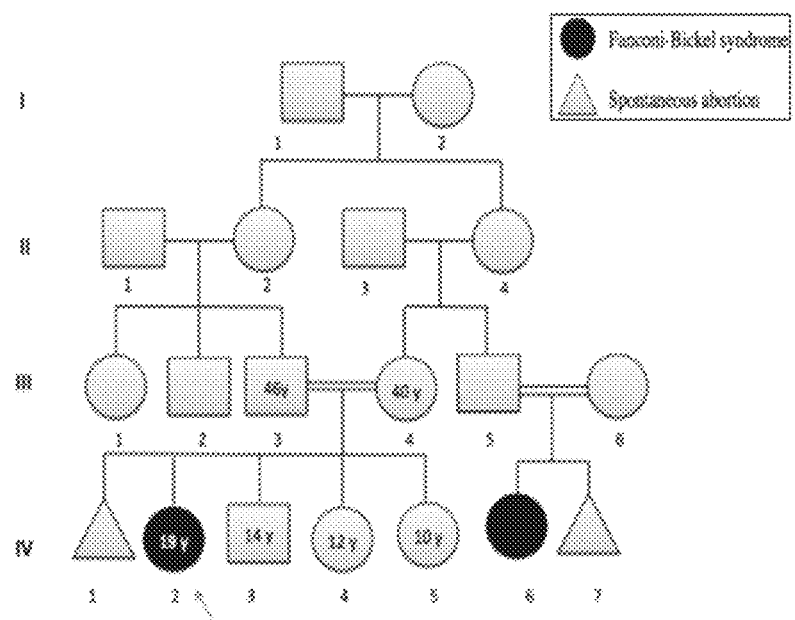
FIG. 4 shows the family pedigree of Patient #2 with FBS and GLUT2 mutation.
Figure 6:
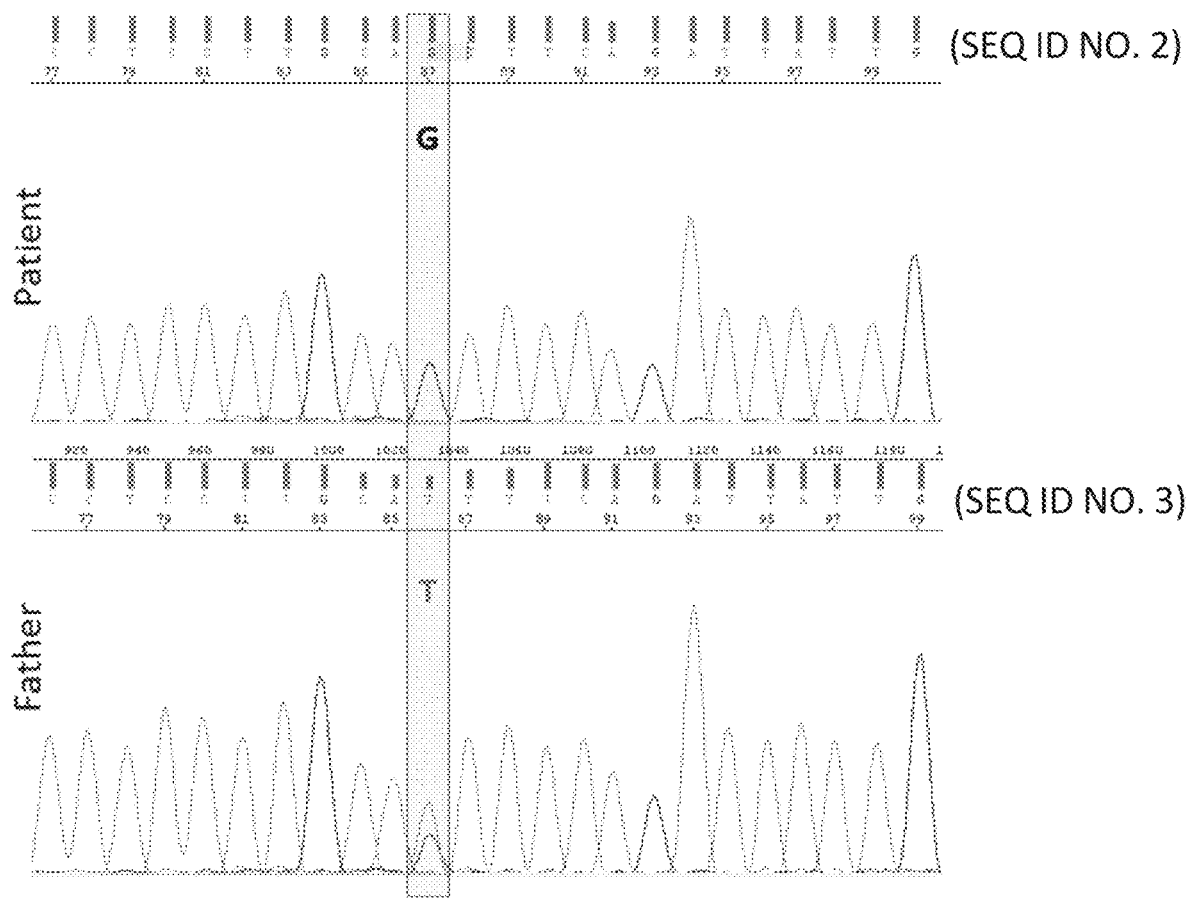
FIG. 6 shows Patient #2 (with GLUT2 mutation) was found to be homozygous for c.613-7T>G: IVS5-7T>G in intron 5 in the SLC2A2 gene.

The Sidra Hospital team had identified Patient #2, with a homozygous mutation in GLUT2 (SLC2A2). Patient #2 was a 19-year-old female, the second child of a first-degree consanguineous parent, presenting with classical features of Fanconi-Bickel syndrome (FBS). The patient was diagnosed with diabetes mellitus at the age of 17 years and was on insulin. The patient presented with renal tubular acidosis, recurrent spontaneous pathological fractures, and a short stature. Biochemical work-up revealed hypophosphatemia, hypocalcemia, elevated alkaline phosphatase and liver enzymes (ALT and AST). Fasting hypoglycemia and postprandial hyperglycemia were also observed. Patient #2's family pedigree is shown in FIG. 4. Whole genome sequencing (WGS) performed at the age of 16 revealed c.613-7T>G: IVS5-7T>G novel mutation in intron 5 of the SLC2A2 gene (FIG. 6).

TABLE 1

Generation of hiPSCs from patients with GLUT2 mutations.

| Subject No. | Associated Disease | Generated iPSC Cell Line | No. of Cell Lines | Phenotype | iPSCs Characterization |
| --- | --- | --- | --- | --- | --- |
| Patient #1 | FBS | Exo_GLUT2 $^{mut}$ iPSC lines | 3 | homozygous c.901C > T mutation in exon 6 of the SLC2A2 gene (NM_000340), resulting in p.Arg301Ter. | Confirmation of mutation, identity authentication (STR), karyotyping, mycoplasma free, virus free, and pluripotency capacity. |
| Patient #2 | FBS | Int_GLUT2$^{mut}$ iPSC lines | 3 | Homozygous mutation for c.613-7T > G: IVS5-7T > G in intron 5 in the SLC2A2 gene. | Confirmation of mutation, identity authentication (STR), karyotyping, mycoplasma free, virus free, and pluripotency capacity. |
| Carrier for Patient #2 | (Carrier) Sister of Patient #2 | Int_GLUT2$^{hetero}$ iPSC lines | 3 | Heterozygous mutation for c.613-7T > G: IVS5-7T > G in intron 5 in the SLC2A2 gene. | Confirmation of mutation, identity authentication (STR), karyotyping, mycoplasma free, virus free, and pluripotency capacity. |

Figure 7:
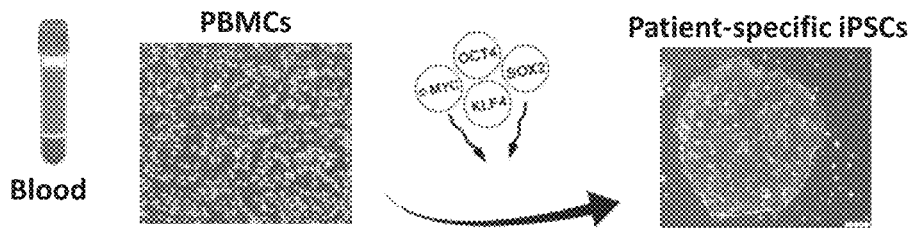
FIG. 7 depicts the generation of hiPSCs from Patients #1 and #2 with GLUT2 mutations.
Figure 7:
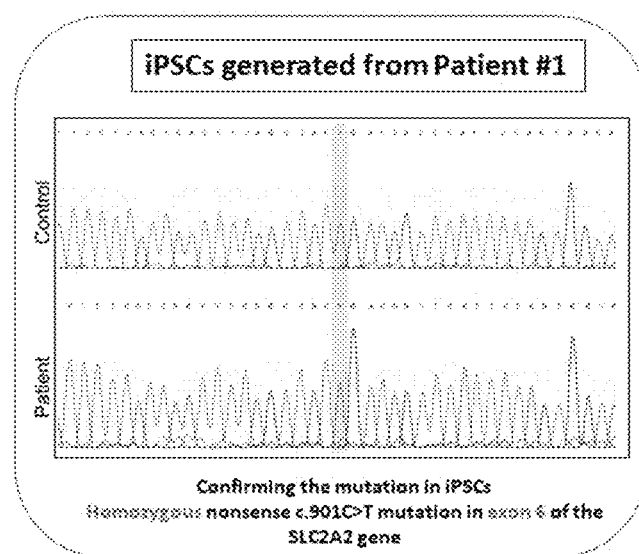
Figure 7:
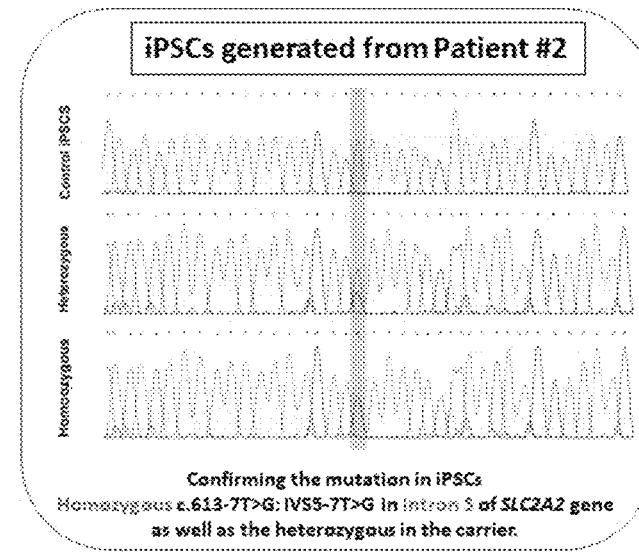
Figure 8:
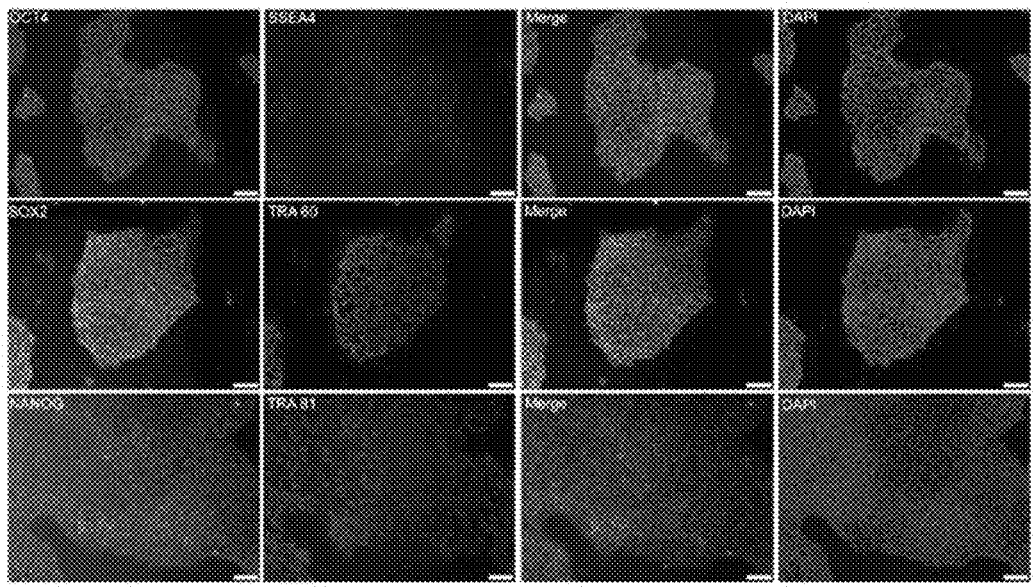
FIG. 8 shows the characterization of hiPSCs from Patient #1 with GLUT2 mutation.
Figure 9A:
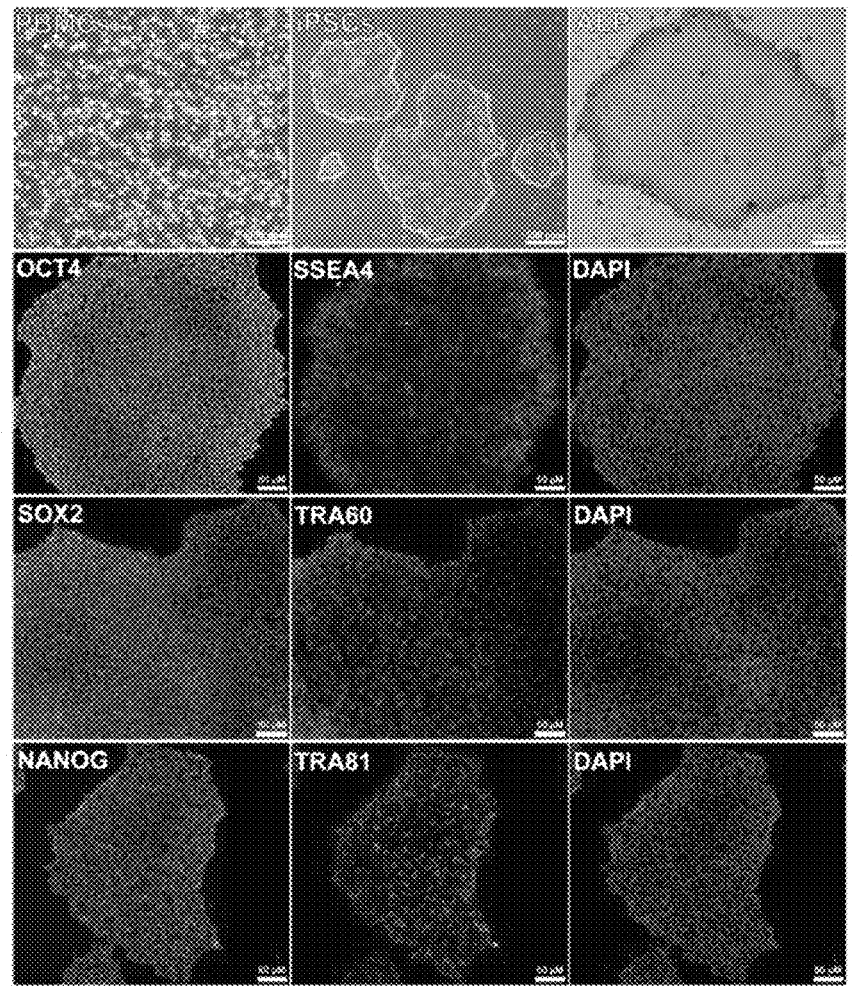
FIGS. 9A and 9B, show the characterization of hiPSCs from Patient #2 with GLUT2 mutation.
Figure 9B:
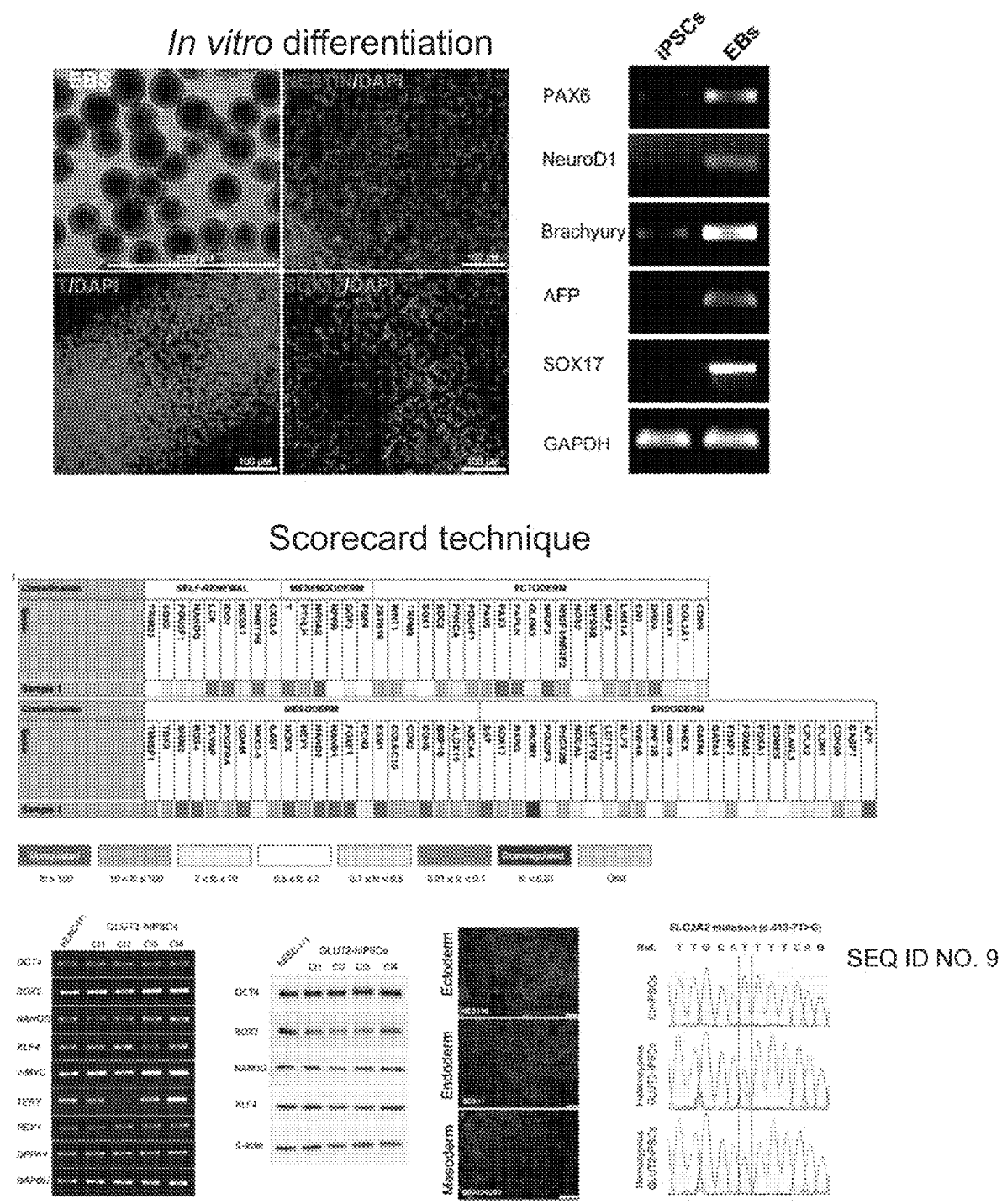
Figure 10:
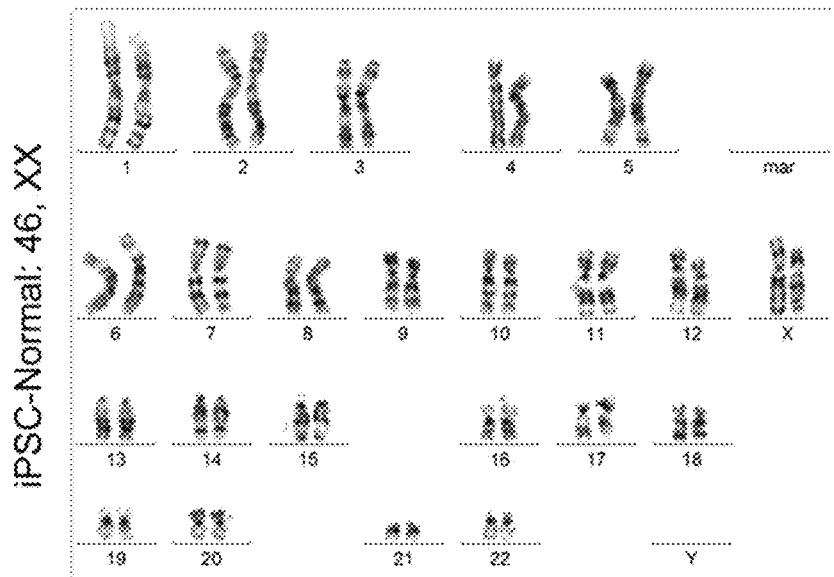
FIG. 10 shows karyotyping of hiPSCs from Patient #2 with GLUT2 mutation.

Blood samples from two patients, Patient #1 and Patient #2, were used to generate hiPSCs (FIGS. 1 and 7) were obtained from the patient a homozygous mutation in GLUT2 (SLC2A2) gene and her sister (carrier), carrying GLUT2 heterozygous mutation. For hiPSC generation, peripheral blood mononuclear cells (PBMCs) were isolated using Ficoll method and were cultured for at least 4 days in StemPro-34 media with cytokines. We used CytoTune-iPS 2.0 Sendai Reprogramming Kit (Thermo Fisher Scientific) to reprogram the PBMCs into pluripotency. 15-30 days after reprogramming, several hESC-like colonies were transferred into separate Matrigel-coated plates. Different clones were exposed to several characterization techniques, including immunostaining, RT-PCR, Western blotting, karyotyping, alkaline phosphatase, and direct and spontaneous differentiation. Our results showed that the hiPSC clones expressed the pluripotency markers OCT4, SOX2, NANOG, SSEA4, TRA60 and TRA81 (FIGS. 8 and 9A). All the hiPSC clones showed hESC-like morphology (FIGS. 8 and 9A) and were stained positive for alkaline phosphatase. Karyotyping analysis confirmed that all the generated hiPSC clones have normal karyotype (FIG. 10). The pluripotency was also confirmed by other techniques, including RT-PCR and Western blotting, which was compared with hESC-H1 (WiCell Research Institute). The results confirmed those obtained by the immunostaining. Also, we differentiated the generated hiPSC lines into the three germ layers, including ectoderm, mesoderm, and endoderm (FIG. 9B).

Example 2

Figure 11:
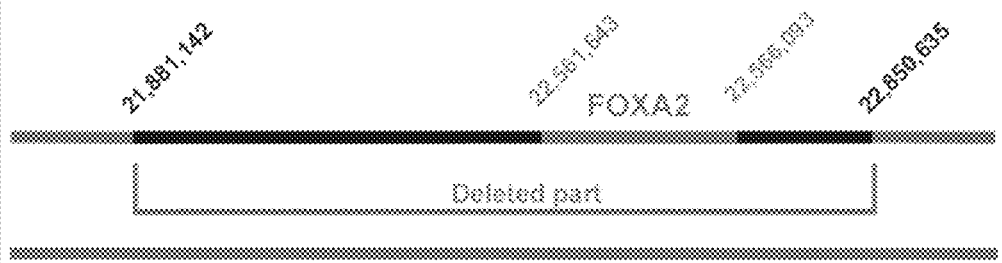
FIG. 11 depicts the extent of deletion (a 969 Kb deletion of chromosome 20 at bands p11.22 to p11.21) in the FOXA2 locus in the patient with the heterozygous deletion encompassing FOXA2 as obtained by microarray analysis.
Figure 12:
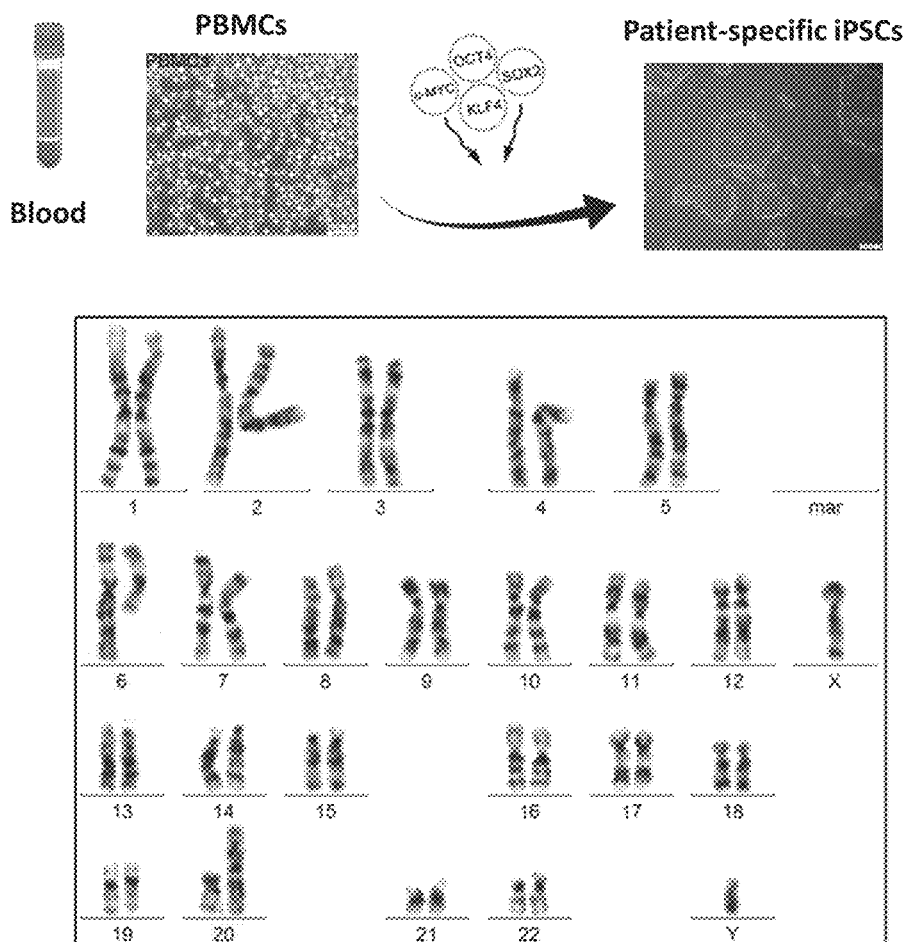
FIG. 12 shows the generation of hiPSCs from the patient with a heterozygous deletion of the FOX2A gene as well as karyotyping.
Figure 13A:
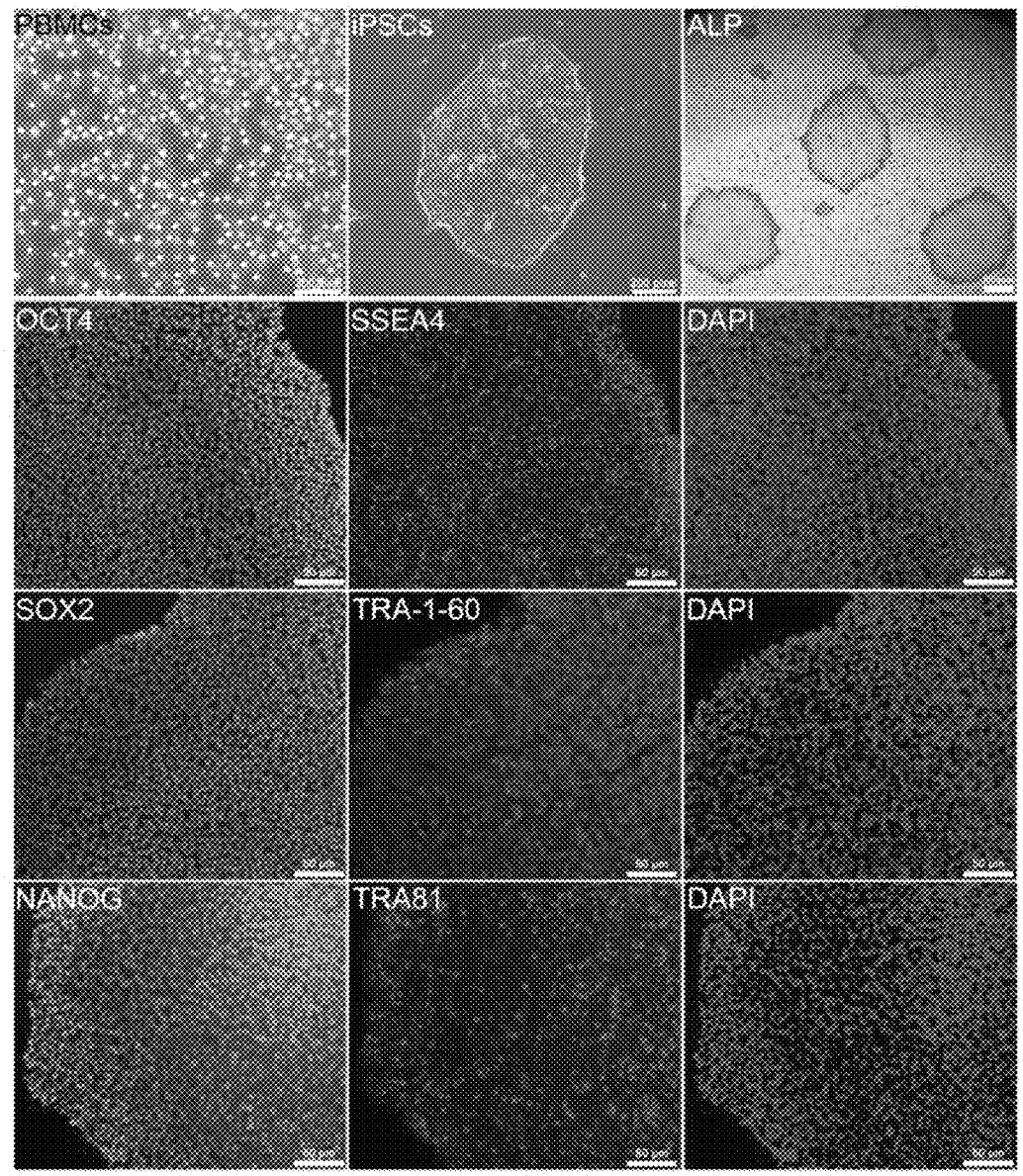
FIGS. 13A and 13B show the characterization of hiPSCs from the patient with the heterozygous deletion of FOX2A. 13A shows Immunostaining images showing the expression of pluripotency markers. 13B shows the generated hiPSCs expressed the pluripotency marker proteins (upper left), differentiation into three germ layers, ectoderm, mesoderm, and endoderm (upper right) and Scorecard analysis showing the differentiation into all three germ layers (lower panel).
Figure 13B:
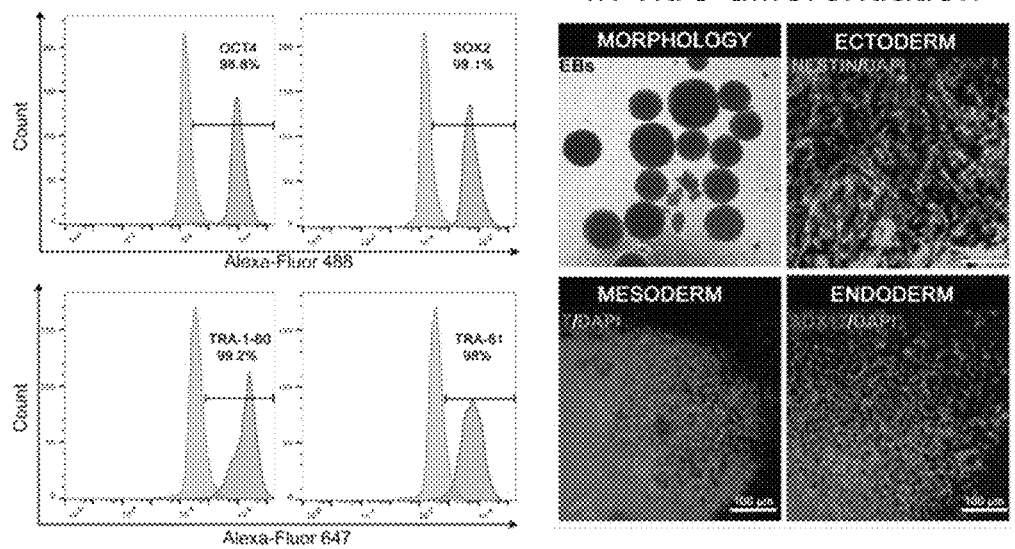
Figure 13B:
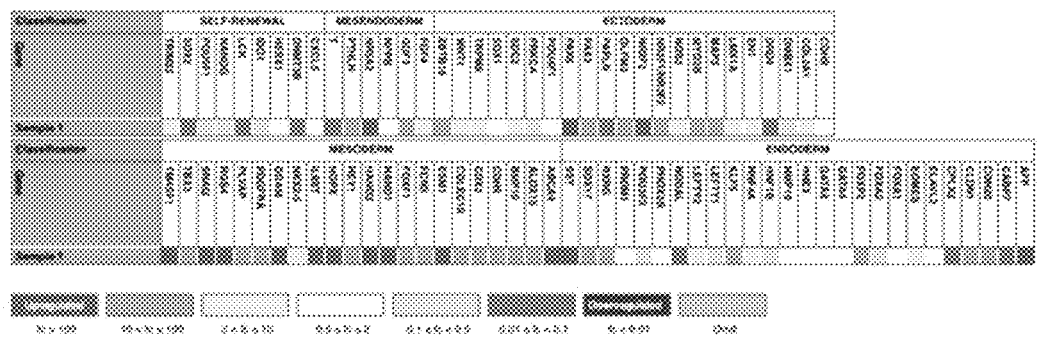
Figure 14:
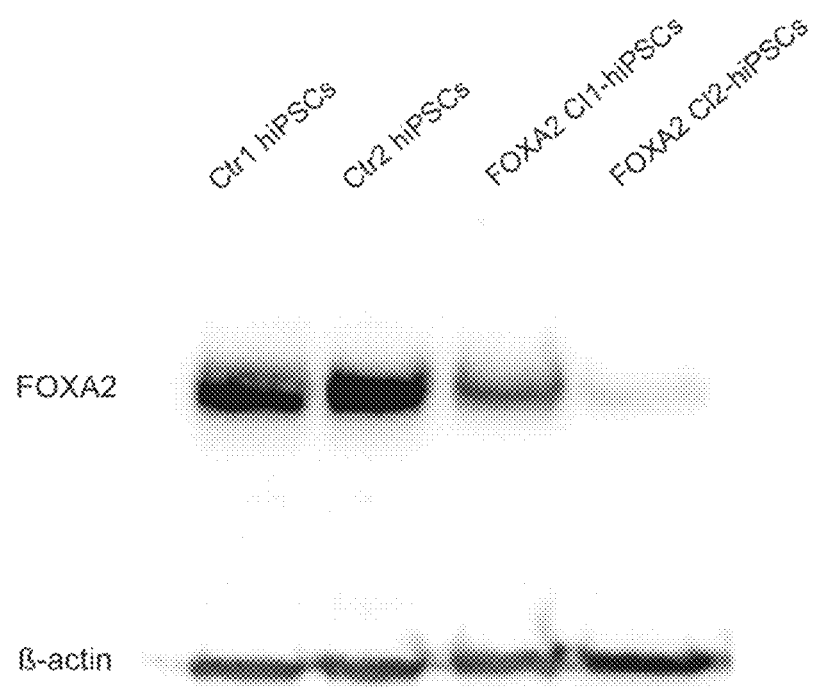
FIG. 14 shows reduced levels of FOXA2 protein in hiPSC cells with the heterozygous deletion of FOXA2 (right two lanes) as compared to controls (left two lanes).

A study identified a patient who presented at the age of 4 years with short stature and was noted previously to have multiple dysmorphic features. Investigations confirmed growth hormone deficiency and central hypothyroidism. The patient had poor weight gain and repeated episodes of abdominal pain, vomiting, and diarrhea. The patient was on levothyroxine and somatropin injection. Microarray analysis detected a male profile with a −969 Kb deletion of chromosome 20 at bands p11.22 to p11.21, shown in FIG. 11. The deletion contains FOXA2 (HNF3β) gene. The smallest described de novo proximal 20p11.2 deletion in a 4-years old boy with dysmorphic features, growth hormone deficiency and central hypothyroidism associated with a complex chromosomal rearrangement involving the short arm of chromosome 20 and FOXA2 (FIG. 12). Subsequent generation of hiPSCs and their characterization are shown in FIGS. 13A, 13B, and 14.

Blood samples were obtained from the patient and used to generate human induced pluripotent stem cells.

Peripheral blood mononuclear cells (PBMCs) were isolated using Ficoll method and were cultured for 5 days in StemPro-34 media with cytokines. We used CytoTune-iPS 2.0 Sendai Reprogramming Kit (Thermo Fisher Scientific) to reprogram the PBMCs into pluripotency. 15-30 days after reprogramming, several hESC-like colonies were transferred into separate Matrigel-coated plates. Different clones were exposed to several characterization techniques, including immunostaining, RT-PCR, Western blotting, karyotyping, alkaline phosphatase, and direct and spontaneous differentiation. Our results showed that the hiPSC clones expressed the pluripotency markers OCT4, SOX2, NANOG, SSEA4, TRA60 and TRA81 (FIG. 13A). All the hiPSC clones showed hESC-like morphology (FIG. 13A) and were stained positive for alkaline phosphatase. Karyotyping analysis confirmed abnormalities in chromosome 20 in all the generated hiPSC clones (FIG. 12). The pluripotency was also confirmed by other techniques, including RT-PCR and flow cytometry, which was compared with hESC-H1 (WiCell Research Institute). Also, we differentiated the generated hiPSC lines into the three germ layers, including ectoderm, mesoderm, and endoderm (FIG. 13B). After characterization, three hiPSC lines were maintained from each sample. The generated FOXA2+/−hiPSCs were further differentiated into pancreatic beta cells to understand the role of FOXA2 in the pancreas development.

The invention claimed is:

1. A method of generating human induced pluripotent stem cells (hiPSCs) with a mutation in both copies of a GLUT2 (SLC2A2) gene comprising:
   obtaining peripheral blood mononuclear cells (PBMCs) from a patient with diabetes mellitus and Fanconi-Bickel syndrome;
   determining whether the PBMCs have a mutation in intron 5 in both copies of the GLUT2 (SLC2A2);
   selecting the PBMCs having the mutation in intron 5 in both copies of the GLUT2 (SLC2A2) gene; and
   exposing the PBMCs from the patient to a means for inducing pluripotency by transducing with vectors capable of conferring expression of OCT4, Sox2, Klf4, and c-Myc,
   wherein the mutation in intron 5 of the GLUT2 (SLC2A2) gene is a c.613-7T>G:IVS5-7T>G mutation.

2. The method of claim 1, wherein the generated hiPSCs are for researching the development and pathologies of diabetes and Fanconi-Bickel syndrome.

* * * * *